US00PP30743P2

(12) United States Plant Patent
Koot et al.

(10) Patent No.: US PP30,743 P2
(45) Date of Patent: Jul. 23, 2019

(54) **NEW GUINEA *IMPATIENS* PLANT NAMED 'DOIMTAMANEFLA'**

(50) Latin Name: *Impatiens hawkeri*
Varietal Denomination: Doimtamanefla

(71) Applicant: DUMMEN GROUP B.V., De Lier (NL)

(72) Inventors: Arjan Koot, Oeffelt (NL); Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/932,834

(22) Filed: May 1, 2018

(51) Int. Cl.
*A01H 5/02* (2018.01)

(52) U.S. Cl.
USPC ..... Plt./318.6

(58) Field of Classification Search
USPC ..... Plt./318.6
See application file for complete search history.

*Primary Examiner* — Annette H Para
(74) *Attorney, Agent, or Firm* — C. A. Whealy

(57) ABSTRACT

A new and distinct cultivar of *Impatiens* plant named 'Doimtamanefla' characterized by its upright, outwardly spreading and mounding plant habit; moderately vigorous growth habit; freely branching habit; dark green-colored leaves; freely and early flowering habit; relatively large red purple and light red bi-colored flowers; and good garden performance.

1 Drawing Sheet

Botanical designation: *Impatiens hawkeri.*
Cultivar denomination: 'DOIMTAMANEFLA'.

BACKGROUND OF THE INVENTION

The present invention relates to a new and distinct cultivar of New Guinea *Impatiens* plant, botanically known as *Impatiens hawkeri* and hereinafter referred to by the name 'Doimtamanefla'.

The new *Impatiens* plant is a product of a planned breeding program conducted by the Inventors in Koka, Ethiopia and Rheinberg, Germany. The objective of the breeding program is to create new early and freely flowering New Guinea *Impatiens* plants with large attractive flowers and good garden performance.

The new *Impatiens* plant originated from a cross-pollination made by the Inventors in November, 2012 in Koka, Ethiopia of a proprietary selection of *Impatiens hawkeri* identified as code number NN10-003550-005, not patented, as the female, or seed, parent with a proprietary selection of *Impatiens hawkeri* identified as code number NN-1184, not patented, as the male, or pollen, parent. The new *Impatiens* plant was discovered and selected by the Inventors as a single flowering plant from within the progeny of the stated cross-pollination in a controlled greenhouse environment in Rheinberg, Germany in April, 2013.

Asexual reproduction of the new *Impatiens* plant by terminal vegetative cuttings in a controlled greenhouse environment in Rheinberg, Germany since June, 2013 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Doimtamanefla'. These characteristics in combination distinguish 'Doimtamanefla' as a new and distinct *Impatiens* plant:

1. Upright, outwardly spreading and mounding plant habit.
2. Moderately vigorous growth habit.
3. Freely branching habit.
4. Dark green-colored leaves.
5. Freely and early flowering habit.
6. Relatively large red purple and light red bi-colored flowers.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are more mounding than plants of the female parent selection.
2. Plants of the new *Impatiens* have larger flowers than plants of the female parent selection.
3. Plants of the new *Impatiens* and the female parent selection differ in flower color as plants of the female parent selection have dark red-colored flowers.

Plants of the new *Impatiens* can be compared to plants of the male parent selection. Plants of the new *Impatiens* differ primarily from plants of the male parent selection in the following characteristics:

1. Plants of the new *Impatiens* have larger flowers than plants of the male parent selection.
2. Plants of the new *Impatiens* and the male parent selection differ in flower color as plants of the male parent selection have rose red and orange red bi-colored flowers.

Plants of the new *Impatiens* can be compared to plants of *Impatiens hawkeri* 'Duepetnn11', disclosed in U.S. Plant Pat. No. 23,946. In side-by-side comparisons, plants of the new *Impatiens* differ primarily from plants of 'Duepetnn11' in the following characteristics:

1. Leaves of plants of the new *Impatiens* and 'Duepetnn11' differ in lower surface color as lower surfaces of leaves of plants of 'Duepetnn11' are red purple in color.
2. Plants of the new *Impatiens* flower later than plants of 'Duepetnn11'.
3. Plants of the new *Impatiens* have larger flowers than plants of 'Duepetnn11'.
4. Plants of the new *Impatiens* and 'Duepetnn11' differ in flower color as plants of 'Duepetnn11' have red purple-colored flowers.

Plants of the new *Impatiens* can also be compared to plants of *Impatiens hawkeri* 'Duemagfi', disclosed in U.S. Plant Pat. No. 23,912. In side-by-side comparisons, plants of the new *Impatiens* differ primarily from plants of 'Duemagfi' in the following characteristics:

1. Plants of the new *Impatiens* have larger flowers than plants of 'Duemagfi'.
2. Plants of the new *Impatiens* and 'Duemagfi' differ in flower color as plants of 'Duemagfi' have light red-colored flowers.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph at the bottom of the sheet comprises a side perspective view of a typical flowering plant of 'Doimtamanefla' grown in a container.

The photograph at the top of the sheet is a close-up view of a typical flowering plant of 'Doimtamanefla'.

DETAILED BOTANICAL DESCRIPTION

The aforementioned photographs and following observations, measurements and values describe plants grown during the winter in 16.5-cm containers in a polyethylene-covered greenhouse in Encinitas, Calif. and under cultural practices typical of commercial New Guinea *Impatiens* production. During the production of the plants, day temperatures averaged 26° C., night temperatures averaged 18° C. and light levels ranged from 4,500 to 5,500 lux. Plants were 25 weeks old when the photographs and description were taken. In the following description, color references are made to The Royal Horticultural Society Colour Chart, 2007 Edition, except where general terms of ordinary dictionary significance are used.

Botanical classification: *Impatiens hawkeri* 'Doimtamanefla'.

Parentage:

*Female, or seed, parent*.—Proprietary selection of *Impatiens hawkeri* identified as code number NN10-003550-005, not patented.

*Male, or pollen, parent*.—Proprietary selection of *Impatiens hawkeri* identified as code number NN-1184, not patented.

Propagation:

*Type*.—By terminal vegetative cuttings.

*Time to initiate roots, summer and winter*.—About five to seven days at temperatures about 20° C.

*Time to produce a rooted young plant, summer and winter*.—About three to four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Upright to outwardly spreading and mounding plant habit; freely branching habit with about eight to ten primary lateral branches each with about four to six secondary lateral branches developing per plant; moderately vigorous growth habit and moderate to rapid growth rate.

*Height, soil level to top of foliar plane*.—About 22.5 cm.

*Height, soil level to top of floral plane*.—About 23.5 cm.

*Plant diameter or spread*.—About 52 cm.

Lateral branch description:

*Length*.—About 19 cm.

*Diameter, primary lateral branches*.—About 1.3 cm.

*Diameter, secondary lateral branches*.—About 8 mm.

*Internode length*.—About 5 cm.

*Strength*.—Strong.

*Aspect*.—About 15° to 45° from vertical.

*Texture and luster*.—Smooth, glabrous; semi-glossy.

*Color, when developing*.—Close to 183B.

*Color, fully developed*.—Close to 187A.

Leaf description:

*Arrangement*.—Opposite or in whorls of four to six leaves; simple.

*Length*.—About 12 cm.

*Width*.—About 4.2 cm.

*Shape*.—Elliptical.

*Apex*.—Acuminate.

*Base*.—Attenuate.

*Margin*.—Entire with ciliation.

*Texture and luster, upper surface*.—Smooth, glabrous; slightly glossy.

*Texture and luster, lower surface*.—Smooth, glabrous; matte.

*Venation pattern*.—Pinnate; arcuate.

*Color*.—Developing leaves, upper and lower surfaces: Close to 146A. Fully expanded leaves, upper surface: Close to 147A; venation, close to 148C. Fully expanded leaves, lower surface: Close to 146B; venation, close to 185A.

*Petioles*.—Length: About 2.2 cm. Diameter: About 3 mm. Strength: Strong. Texture, upper and lower surfaces: Smooth, glabrous; slightly glossy. Color, upper surface: Close to 185A to 185B. Color, lower surface: Close to 183B.

Flower description:

*Flower type and flowering habit*.—Relatively large single rounded to axillary flowers; freely flowering habit, typically about 140 flowers developing per plant; flowers positioned above and beyond the foliar plane; flowers typically face mostly upright to outwardly.

*Flower longevity*.—Flowers typically last about two to three days on the plant under greenhouse conditions; petals self-cleaning, gynoecium persistent.

*Fragrance*.—None detected.

*Natural flowering season*.—Year-round under greenhouse conditions; in the garden, flowering continuous from spring until fall in California; early flowering habit, plants typically begin flowering about twelve weeks after planting.

*Flower buds*.—Length: About 2.8 cm. Diameter: About 1.7 cm. Shape: Ovate. Texture and luster: Smooth, glabrous; slightly glossy. Color: Close to 53C.

*Flower diameter*.—About 8 cm.

*Flower depth*.—About 2.4 cm; with spur, about 8.2 cm.

*Petals*.—Quantity and arrangement: Five per flower in a single whorl. Banner petals, length: About 3.8 cm. Banner petals, width: About 6.2 cm. Lateral petals, length: About 3.8 cm. Lateral petals, width: About 4.8 cm. Lower petals, length: About 4.8 cm. Lower petals, width: About 5.5 cm. Shape: Cordate. Apex: Emarginate. Base: Attenuate. Margin: Entire; margins tend to recurve. Texture and luster, upper and lower surfaces: Smooth, glabrous; velvety; matte. Color: When opening, upper surface: Center and towards the base, close to N74A; towards the apex and margins, close to 53B. When opening, lower surface: Center and towards the base, close to N66C; towards the apex and margins, close to 45C. Fully opened, upper surface: Center and towards the base, close to N74A to N74B; towards the apex and margins, close to 46C to 46D; venation, close to N74A; color does not fade with development. Fully opened, lower surface: Towards the apex and margins, close to 46D transitioning towards the base to 47C to 47D, 63B and N74D; venation, close to 63B; with development, color becoming closer to 47C to 47D and towards the base, close to N74D.

*Sepals*.—Quantity and arrangement: Three in a single whorl; two lateral sepals and one center sepal modified into an elongated spur. Lateral sepals, length: About 1.2 cm. Lateral sepals, width: About 7 mm. Center sepals, length: About 2.2 cm. Center sepals, width: About 1.5 cm. Shape: Elliptical. Apex: Acuminate. Base, lateral sepals: Truncate. Base, center sepal: Modified into a curved spur, fused into a slender tube. Margin: Entire. Texture and luster, upper and lower surfaces: Smooth, glabrous; slightly glossy. Color: When opening, upper surface: Close to 145C. When opening, lower surface: Close to 146B. Fully opened, upper surface: Close to 73C to 73D; towards the apex, close to N74B. Fully opened, lower surface: Close to 68C. Spur length: About 6 cm. Spur diameter: At the flower, about 2 mm. Spur texture and luster: Smooth, glabrous; slightly glossy. Spur color: Close to 59B.

*Peduncles*.—Length: About 4.5 cm. Diameter: About 2 mm. Angle: About 45° from branch axis. Strength: Strong. Texture and luster: Smooth, glabrous; slightly glossy. Color: Close to 59A.

*Reproductive organs*.—Stamens: Quantity: Five fused at anthers; filaments free. Filament length: About 2 mm. Filament color: Close to 47A. Anther size: About 3 mm by 6 mm. Anther shape: Oblong. Anther color: Close to 161B. Pollen amount: Moderate. Pollen color: Close to 158B. Pistils: Quantity per flower: One. Pistil length: About 7 mm. Stigma diameter: About 2 mm. Stigma shape: Rounded. Stigma color: Close to 157A. Style length: About 1 mm. Style color: Close to 157A. Ovary color: Close to 146A.

*Seeds and fruits*.—To date, seed and fruit production has not been observed on plants of the new *Impatiens* to date.

Pathogen & pest resistance: To date, plants of the new *Impatiens* have not been observed to be resistant to pathogens and pests common to *Impatiens* plants to date.

Garden performance: Plants of the new *Impatiens* have been observed to have good garden performance and tolerate temperatures ranging from about 5° C. to about 40° C.

It is claimed:

1. A new and distinct *Impatiens* plant named 'Doimtamanefla' as illustrated and described.

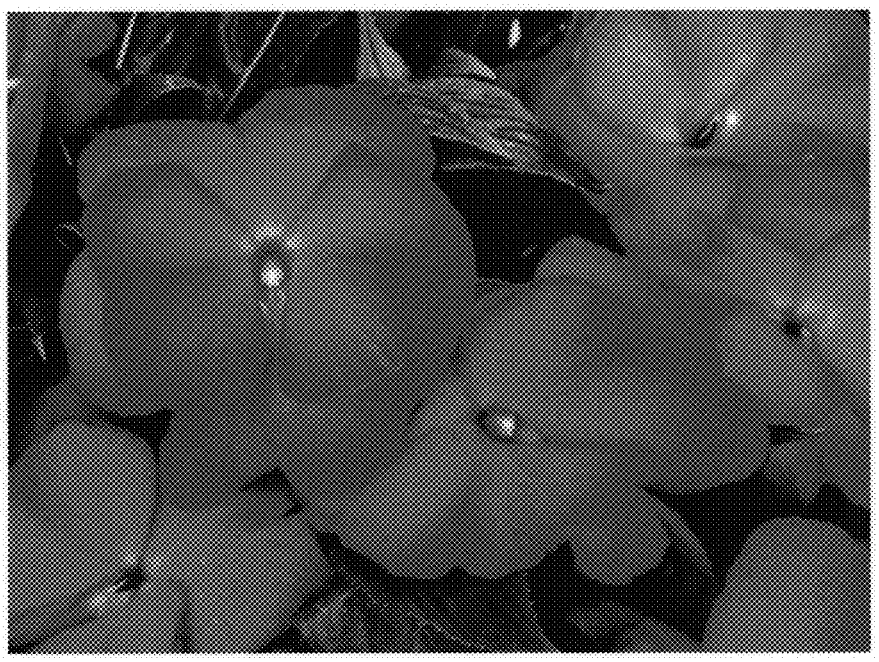
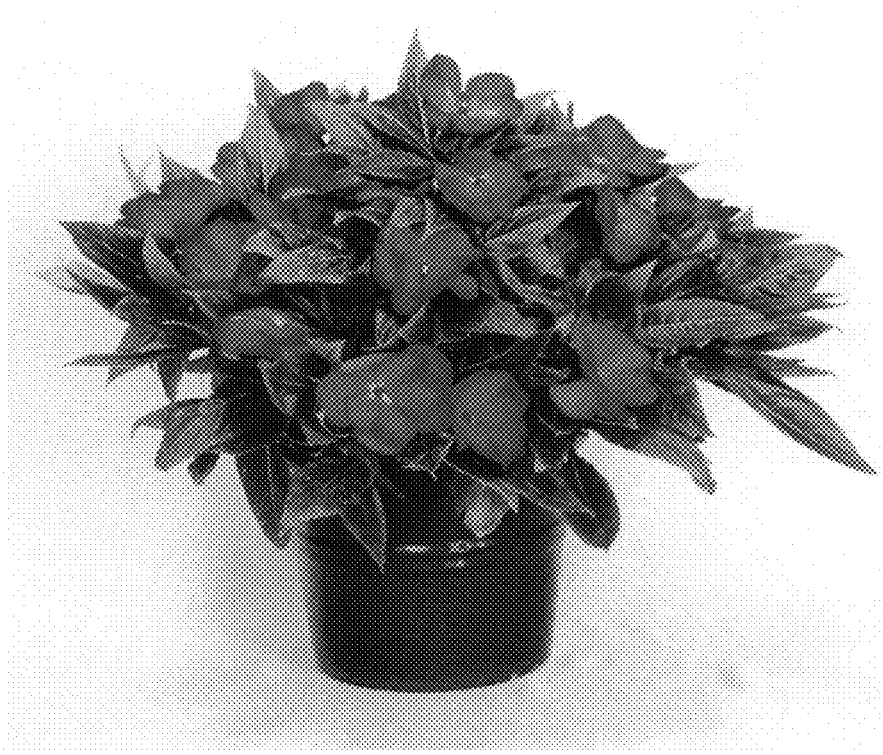

* * * * *